United States Patent [19]

William

[11] Patent Number: 4,697,582
[45] Date of Patent: Oct. 6, 1987

[54] APPLIANCE FOR CORRECTING RACHIDIAL DEFORMITIES

[76] Inventor: Pezé William, 16 rue de Jerrapes, 78800 Houilles, France

[21] Appl. No.: 664,225

[22] Filed: Oct. 24, 1984

[30] Foreign Application Priority Data

Oct. 28, 1983 [FR] France .................. 83 17289

[51] Int. Cl.⁴ .............................................. A61F 5/00
[52] U.S. Cl. ..................................................... 128/69
[58] Field of Search .................. 128/92 E, 69, 92 EA, 128/78

[56] References Cited

U.S. PATENT DOCUMENTS

| 3,760,056 | 9/1973 | Rudy . | |
|---|---|---|---|
| 4,041,939 | 8/1977 | Hall | 128/69 |
| 4,047,524 | 9/1977 | Hall | 128/69 |
| 4,269,178 | 5/1981 | Keene | 128/69 |
| 4,289,123 | 9/1981 | Dunn | 128/84 |
| 4,527,554 | 7/1985 | Klein | 128/69 |

FOREIGN PATENT DOCUMENTS

| 3032237 | 3/1982 | Fed. Rep. of Germany . |
| 2275679 | 1/1976 | France . |
| 2516788 | 5/1983 | France . |
| 780652 | 8/1957 | United Kingdom . |

OTHER PUBLICATIONS

Scientific American—Nov. 1979—Shape Memory Alloys, p. 79.

Primary Examiner—Gene Mancene
Assistant Examiner—Wenceslao I. Contreras
Attorney, Agent, or Firm—Pearne, Gordon, McCoy & Granger

[57] ABSTRACT

An appliance for the dynamic correction of rachidial deformities, wherein in the deformed part of the rachis which it is wished to correct is implanted a mechanical assembly of biocompatible material comprising screwed onto each vertebra of the deformed area, in the angle formed by the spinous process and the disk, a retaining clamp having at least one guidance opening from one side to the other parallel to the axis of the rachis; an elastic restoring or return structure having at least one elastic rod with a shape memory of the corresponding part of a normal rachis and introduced into the aforementioned guidance openings of the retaining clamp fixed to each vertebra, immobilized in rotation in each guidance opening and in translation on one of the retaining clamps.

7 Claims, 9 Drawing Figures

APPLIANCE FOR CORRECTING RACHIDIAL DEFORMITIES

BACKGROUND OF THE INVENTION

The present invention relates to an appliance for correcting rachidial deformities and essentially scoliosis, which is the major cause of such deformities.

The appliance is intended to be surgically implanted along the deformed part of the rachis or vertebral column of a growing child and to remain there a number of months or years during which it exerts a corrective mechanical action on the profile of the rachis for reducing the initial deformity. When growth is at an end or when the correction obtained is satisfactory, surgery takes place again in order to remove the appliance.

Scoliosis is a disease which deforms the rachis and reaches one or more rarely two segments thereof during the growth period. This deformity is particularly serious because, due to the fact that it combines a horizontal torsion and a flexion in a frontal plane, it develops in the three dimensions in space. It is also an evolutive disease, which starts during the growth phase, probably due to the rotation of one or two vertebral bodies. Scoliosis is in particular an evolutive dynamic disease and several known tests (particularly the bending test) show its at least partially correctable nature at the start of the disease. The deformity subsequently has a tendency to become fixed as a result of the stiffening of the articular parts and deformities of the osseous parts. It is therefore important to correct this deformity as early as possible after its detection.

The presently known treatments for scoliosis are firstly orthopedic and dynamic (wearing a rigid corset, traction exerted on the vertebral column particularly by suspending the patient by the head and kinesitherapy). Surgery is carried out if this treatment is inadequate and the deformity is aggravated. The object of the surgery is, after reducing to the maximum possible extent the deformities, to fix the lesions by means of rigid equipment and arthrodesis to prevent aggravation of the deformity. These methods are sometimes necessary to avoid the worst, but nevertheless have the serious disadvantage of being definitive and of stopping the deformity by stopping growth.

SUMMARY OF THE INVENTION

The object of the present invention is a process for the dynamic correction of rachidial deformities by a novel and original action mode on the deformities themselves.

According to the present process, a tension and a gentle torque are applied on a permanent basis to the angle formed by the spinous process and the disk of each vertebra of the deformed part of the rachis so as to obtain the slow and progressive correction of flexions and torsions of said part of the rachis, whilst attempting to bring it back to its normal state.

The present invention also relates to an appliance for the dynamic correction of rachidial deformities and particularly scoliosis utilizing the aforementioned process, which makes it possible to cure the same by a gentle, permanent action of a surgically implanted corrective appliance.

Thus, the present invention also specifically relates to an appliance for the dynamic correction of rachidial deformities, wherein in the deformed part of the rachis which it is wished to correct is implanted a mechanical assembly of biocompatible material comprising screwed onto each vertebra of the deformed area, in the angle formed by the spinous process and the disk, a retaining clamp having at least one guidance opening from one side to the other parallel to the axis of the rachis; and an elastic restoring or return structure having at least one elastic rod with a shape memory of the corresponding part of a normal rachis and introduced into the aforementioned guidance openings of the retaining clamp fixed to each vertebra, immobilized in rotation in each guidance opening and in translation on one of the retaining clamps.

The essential feature of the dynamic corrective appliance according to the invention is that it has an elastic restoring structure with a shape memory corresponding to a rachis with a normal profile, whereby to the diseased rachidial segment is permanently applied a tension and a gentle torque with the object of correcting its deformity. There is no doubt, and this is vital, that the permanent nature of a gentle action is much more effective for at least partly bringing about a correction of the rachis profile and preventing the aggravation of a scoliosis, than a violent, sudden action applied for a limited time. Thus, the gentle action resulting from the permanent stressing of the elastic restoring structure retaining in its memory the correct shape in the three dimensions of the corresponding part of a normal rachis is applied to all the components leading to the scoliotic deformity and in particular the rotation and inflexions in the frontal plane. The complete implanted appliance must obviously be made from a biocompatible material. As a non-limitative example, it is possible to choose stainless steel NSM 21 S (Ugine standard). The length and cross-section of the elastic restoring structure having a memory are defined as a function of the age of the patient and the dynamic performances which it is wished to obtain. It is designed to be placed at the bottom of the spinous fossa along the rear part of each diseased vertebra and must obviously be resistant to wear. Moreover, the very principle of the appliance according to the invention, means that the corrective force and the torque applied by the elastic restoring structure to the diseased rachis part are a direct function of the degree of geometrical deformity of said rachis and increase therewith, which is a very important advantage.

The corrective appliance according to the invention is to be used in a preventative rather than a curative capacity and is consequently fitted as early as possible during the evolutive period of the disease, when the deformities of the rachis are still flexible and the osseous parts have still not undergone any deformation. It is therefore necessary for the purpose of choosing the correct moment for applying the appliance according to the invention, to assess at a very early time the existence and evolutive character of an incipient scoliosis.

It is also pointed out that the rods of the elastic restoring structure, which are to some extent the active element of the corrective appliance according to the invention, are only slid into the guidance openings of the retaining clamps, so as to permit a completely free axial displacement of each vertebra, thereby enabling the growth of the rachis throughout the implantation period of the appliance. The guidance openings of the retaining clamps have a shape corresponding to the cross-section of the elastic rods excluding the rotation thereof about their axis in order to permit the application of torsional stresses, which would not be possible if the rods were able to rotate on themselves in each of the guidance openings. To this end and according to the invention, the guidance openings have a special shape and in particular chosen from oval or polyhedral cross-sections or in the form of rails and crosses. When the guidance openings has an oval cross-section, the major axis of this oval is preferably contained in a sagittal plane. At both their inlet and outlet, the guidance openings of the clamps can have a widened or flared shape, which permits a certain bending of the elastic rod between the different guidance points.

According to the invention, each retaining clamp of the elastic rod is fixed to the associated vertebra by any known means and in particular in accordance with the embodiments described hereinafter.

According to a first embodiment, each retaining clamp is fixed to the associated vertebra by direct screwing into the centro-lateral segment.

According to a second embodiment of the invention, each retaining clamp is fixed to the associated vertebra with the aid of a threaded rod passing through the spinous process and is secured on the other face thereof by a nut applying a bearing plate, which is located in the rear vertebral arch.

According to a third embodiment of the invention each retaining clamp is fixed to the associated vertebra by direct screwing into the vertebral pedicle.

In general terms, the three above embodiments are given in an illustrative and non-limitative nature and it is obvious that both the Expert and the surgeon can use any other fixing mode which he considers appropriate in the particular case and in particular any combination of the three aforementioned cases, without passing beyond the scope of the invention.

The above arrangements of the corrective appliance according to the invention permit the application of the corrective tension of the elastic rod or rods to the rear arch of each vertebra to which there is easy access all along the vertebral column. In general terms, the application point of corrective force must be located as close as possible to the vertebral rotation centre in order to have maximum effectiveness with regards to the torques applied. As this centre is located in the spinal canal, for obvious reasons it is not possible to apply a torque thereto. The closest area and also that which has the easiest access by the dorsal tract is the spine-disk angle, so that the corrective torque of the corrective appliance according to the invention is applied to this area. The appliance applies to the same area the restoring force aiming at correcting the pathological frontal curvatures acquired by a deformed rachis.

BRIEF DESCRIPTION OF THE DRAWINGS

The invention is described in greater detail hereinafter relative to non-limitative embodiments and the attached drawings, wherein show.

DETAILED DESCRIPTION OF THE PREFERRED EMBODIMENTS

Figure 1:
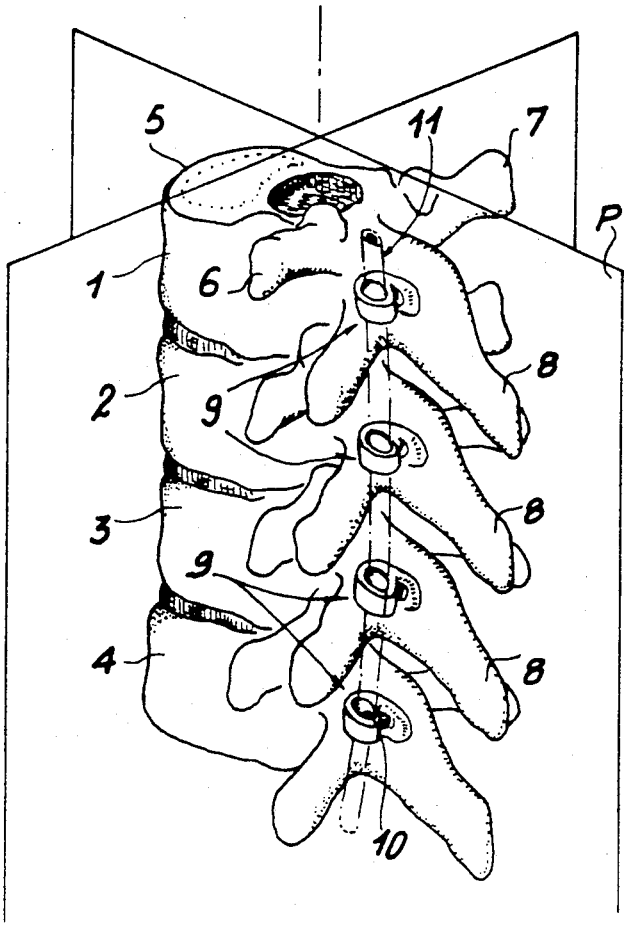
FIG. 1 a general perspective view of the corrective appliance according to the invention, in the case where the elastic restoring structure is constituted by a single elastic rod having a shape memory and which constitutes the active part of the appliance.

FIG. 1 shows four vertebrae 1, 2, 3 and 4 of a rachis portion suffering from a scoliosis-type deformity by turning the drawing to the left relative to the sagittal plane P passing through the axis of vertebra 1. It is possible to see on each vertebra the vertebral body 5 and the transverse processes 6, 7 and spinous process 8. According to the invention, retaining clamps 9, whose shape and fixing will be explained in greater detail with reference to following drawings, are located in the rear vertebral arch between the spinous process 8 and the transverse process 6. In the particular case of FIG. 1, the elastic restoring structure comprises a single rod 11 made from a biocompatible, elastic material. Each retaining clamp 9 is provided with an opening 10, into which is introduced the elastic rod 11 having a shape memory. For reasons of clarity, FIG. 1 only shows rod 11 in a partial manner by means of dotted lines.

The elastic rod 11 has been designed, prior to its implantation in the appliance of FIG. 1, so as to have a shape memory of part of a normal rachis corresponding to vertebrae 1, 2, 3 and 4 of FIG. 1 and consequently precisely exerts the permanent, gentle tension necessary for restoring said vertebrae by flexion and torsion to their correct initial position, i.e. in order to correct the overall rachidial position shown. The guidance openings 10 have a cross-section identical to that of the elastic rod 11 and which is in particular oval, so as to prevent any rotation of rod 11 about its axis in openings 10, thus permitting the torsional action of said rod 11 on the rachis part equipped with the appliance. Moreover, each guidance opening 10 optionally has widened or flared upper and lower ends, so as to permit the harmonious flexion of rod 11 between its different connecting points.

Rod 11, equipped with its different retaining clamps 9, is fixed by a set screw 12 to one of the same, in order to be blocked in longitudinal translation. All the other movements of the rod 11 are consequently permitted and its gentle frictional passage into the retaining clamps 9 makes it possible for the vertebral column of the patient to grow during the complete appliance implantation time.

In FIG. 1, the cross-section of the guidance openings 10 is oval, with a major axis located in a sagittal plane. However, this is not limitative and this cross-section can have a very variable shape, such as polyhedral, or can be shaped like a rail or cross, only a circular cross-section being impossible, because it would permit the rotation of rod 11 about its axis and would cancel out any possibility of a torsional stress thereof on the rachis.

It should also be noted that rod 11 only requires a fixing in translation at one of its retaining flanges, in order to prevent its sliding along the axis. This clamp can, for example, be one of the upper or lower end clamps of the appliance and it is merely necessary to have a small screw passing through the same to secure the rod once the appliance has been fitted.

Figure 2:
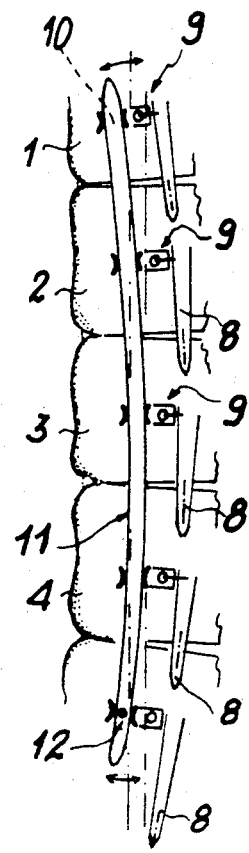
FIG. 2 a side view relative to FIG. 1 of the elastic rod fitted on a deformed portion of the rachis.

FIG. 2 shows a profile view of the corrective appliance of FIG. 1, on which it is possible to see the four vertebrae 1, 2, 3, 4, the elastic rod 11 introduced into the flared oval openings 10 of the different clamps 9. It is also possible to see at 12, the outline of the translation fixing screw of rod 11 on the final clamp 9. FIG. 2 inter alia illustrates the curvature of the elastic rod 11 in a sagittal plane.

In FIGS. 1 and 2, the guidance openings 10 are not strictly cylindrical but, according to the invention, have a flared shape, enabling a certain bending of rod 11 between two consecutive retaining clamps 9. This precaution is indispensable to enable the rod to fulfil its complete function by supplying the vertebral column with the support necessary to permit the correction expected of it. In the same way, the guidance openings 10 have an oval cross-section, whereof the major axis is located in a sagittal plane in order to prevent the rotation of rod 11 on itself and to enable it to exert its torque on each vertebra.

Figure 3:
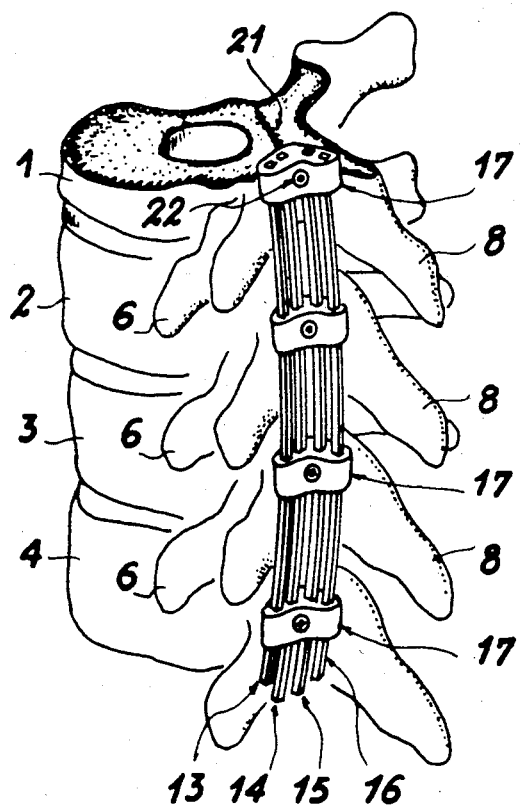
FIG. 3 an embodiment of the invention in the case where the elastic restoring structure is constituted by several parallel elastic rods.

FIG. 3 shows a very interesting variant of the appliance of FIG. 1, in which the elastic restoring structure is constituted by a group of four parallel elastic rods. FIG. 3 shows the same elements as in FIG. 1 and carrying the same reference numerals. The single elastic rod of FIG. 1 is merely replaced by the group of four square, elementary rods 13, 14, 15 16, maintained in place in the spine-vertebral segment angle by retaining clamps 17 having four square openings, whereof each corresponds to one of the elementary rods 13, 14, 15, 16 and which will be described in greater detail relative to FIG. 4.

This embodiment is of particular interest, because it makes it possible to use elastic elementary rods 13, 14, 15, 16 of a thinner or more slender type and whereof the thus formed assembly still has all the necessary elasticity and flexibility. Thus, it is possible either to use completely linear elementary rods 13, 14, 15, 16, or rods which are preshaped to a greater or lesser extent to the profile of a corresponding, normal rachis portion. As in the case of FIG. 1, the thus formed restoring structure exerts in a permanent manner on each vertebra a low intensity torque and force, which is the sought fundamental result for obtaining a progressive correction under good conditions.

Figure 4:
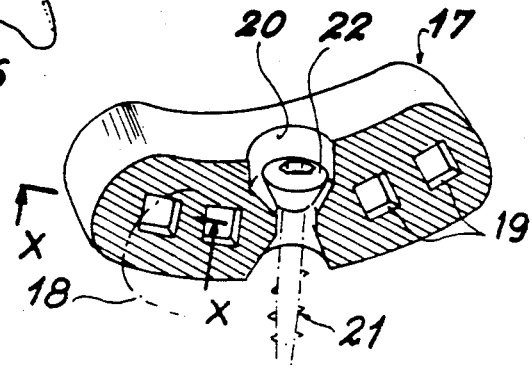
FIG. 4 a constructional detail of the retaining clamps of the embodiment of FIG. 3.

FIG. 4 shows a larger-scale detail of one of the retaining clamps 17 of FIG. 3, whereof the characteristic curvature of the dorsal part 18 is intended to correspond to the concavity of the spinous zone-segment of each vertebra. Part 17 has four openings such as 19, which have a square cross-section and are flared at their upper and lower inlets, as will be shown relative to the following FIG. 5, in order to permit a certain bending of elementary rods 13 to 16 about each clamp 17. FIG. 4 is in fact a section through the centre of the thickness of clamp 17 showing the opening 20 reserved for screwing into the corresponding vertebra with the aid of a screw 21 having a head 22 which is located in the opening 20 of said clamp 17.

Figure 5:
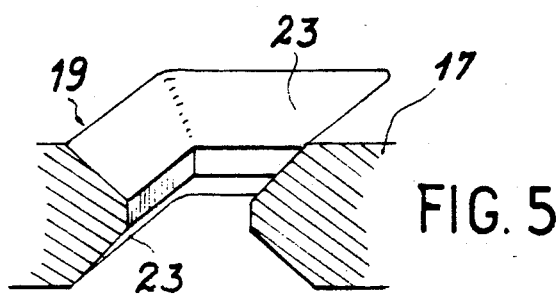
FIG. 5 the flared shape of the square holes in the retaining clamp of the embodiment of FIG. 4.

FIG. 5 is a section along line XX of FIG. 4 of one of the passage holes 19 for the elementary rods 13 to 16, whose flared shape is shown in the form of inclined planes 23 permitting a certain bending of the corresponding elastic restoring rod at the inlet and outlet of each square hole 19.

Figure 6:
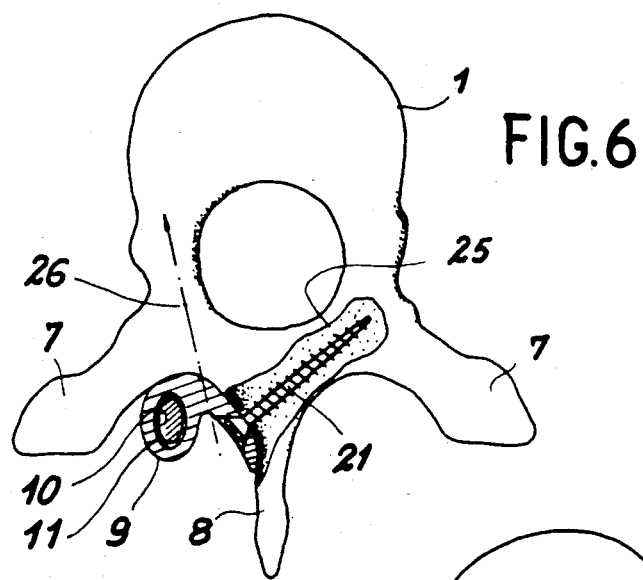
FIGS. 6, 7 and 8 different possible methods for fixing the retaining clamps to the corresponding vertebrae.
Figure 7:
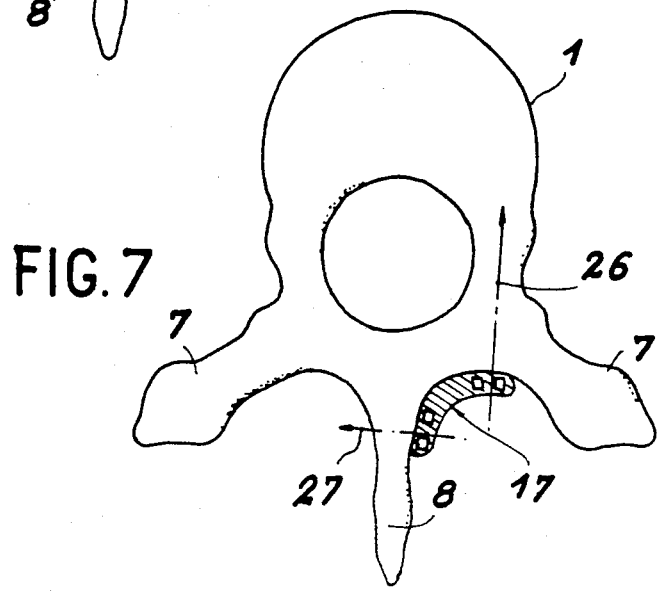
Figure 8:
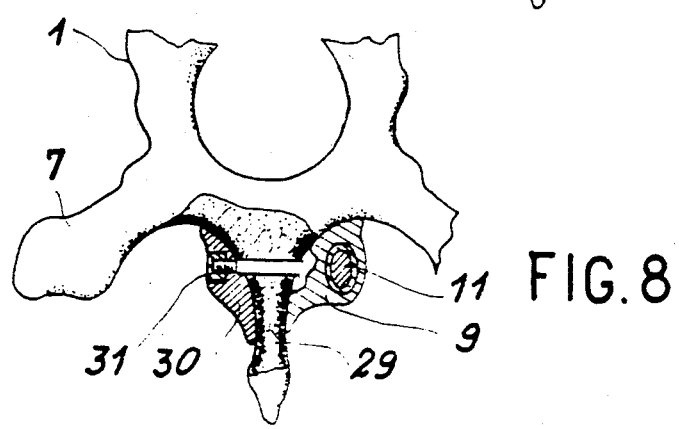

FIGS. 6 to 8 show different shapes and different fixing possibilities for a retaining clamp on the corresponding vertebra 1.

FIG. 6 corresponds to the embodiment of FIG. 1 using a single elastic rod 11 and a retaining clamp 9. The latter is fixed in the vertebral disk 25 with the aid of a screw 21. In a variant, is shown in mixed line diagrammatic form, another possible implantation of screw 21 at 26 in the vertebral pedicle.

In FIG. 7, the retaining clamp 17 corresponding to the embodiment with four elementary rods of FIG. 3, can be fixed as required by screws such as 26 and/or 27, which are either screwed into the vertebral pedicle, or through the spinous process.

Finally, FIG. 8 shows an embodiment having a single elastic rod 11 and a retaining clamp 9, which is fixed by screwing with the aid of screw 28 through the spinous process 29 using a support plate 30, located in the opposite disk-spine angle and which is tightened and prevented from rotation by a nut 31.

In general terms, these different fixing modes which can also be used simultaneously, will be chosen as a function of what is best in each particular case by the surgeon, who will utilize all the resources of the art to choose the best possible solution in each particular case.

Figure 9:
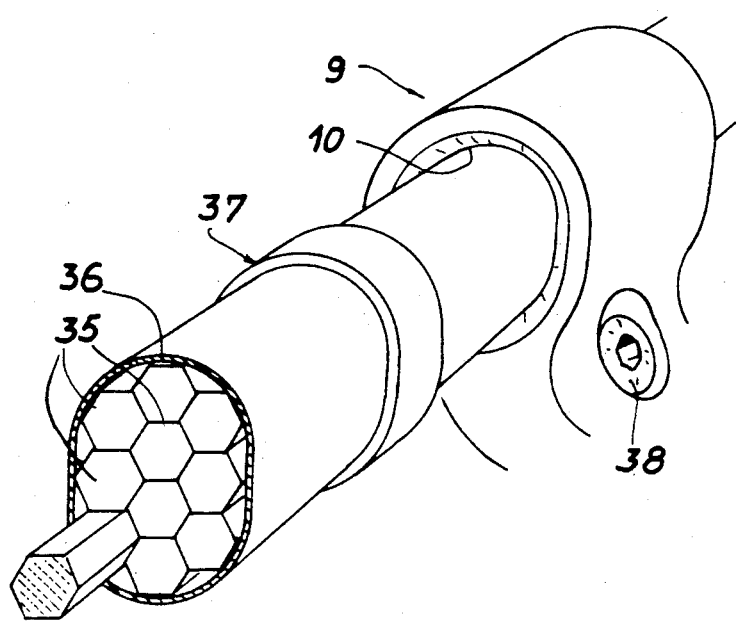
FIG. 9 a special embodiment of the elastic restoring structure of the corrective appliance according to the invention.

FIG. 9 shows another embodiment of the elastic restoring structure of the corrective appliance according to the invention, which has a certain number of polyhedral elementary restoring rods 35, enclosed in a sheath 36 and held in position by retaining rings or collars 37. As in the previous embodiments, a retaining clamp 9 having the flared oval opening 10 surrounds sheath 36 and is fixed with a screw, diagrammatically shown at 38 to the corresponding vertebra.

In the special, non-limitative case of FIG. 9, the construction shown for this elastic restoring structure has ten hexagonal elementary rods in order to fill the interior of sheath 36. In order to improve this system, it would also be possible to envisage providing recesses on the periphery of the lateral faces of the elementary rods 35, so as to decrease the friction coefficient between two adjacent rods, so as to make the elastic structure assembly more flexible.

This embodiment is particularly interesting because it makes it possible to form, with the aid of easily realisable elementary rods, a larger elastic restoring assembly which can be easily preshaped and is also able to produce the restoring torque and forces with the desired intensity with respect to the sought objective.

In all the preceding embodiments, it is possible to use an elastic restoring structure with a linear shape, in which case only the rotations and flexions of the rachis in a frontal plane are corrected. If this is permitted by the bicompatible material used for the structure, it is also possible to preshape it to the profile of a normal vertebral column, thus enabling the corrective appliance, if necessary, to simultaneously act on the rachidial profile in a frontal plane.

The surgical fitting of the dynamic corrective appliance according to the invention takes place in the following way. The patient is firstly placed in ventral decubitus on an ordinary operating table. The surgeon acts on the two spinous fossas and releases the vertebral column up to the articular processes. He then makes the necessary perforations, either of the disk, or of the spinous process by means of a punch on the deformed rachidial segment. An elastic rod of appropriate size and having in its memory the shape of the corresponding part of a healthy rachis is then brought to the appropriate shape on the diseased segment in question. The different retaining clamps are placed on the rod and it is then placed along the rachis of the patient using three special clips and whilst maintaining it in the deformed state. The surgeon then passes the threaded rods into the openings or screws them down in a provisional manner according to the fitting procedure chosen, and also fits the nuts and bearing plates. Once securing and tightening of the assembly has taken place, it is possible to release the clips and the incision is then closed with draining.

The patient must get up immediately and, as it is usually a question of a growing child, he can resume schooling as soon as healing has taken place because no internal traumatism is caused by the fitting of this corrective appliance. It is also recommended that the child carries a lombostat in an almost permanent manner throughout the time when the corrective appliance is fitted to the rachis, in order to limit wear to the parts present as a result of the clearance of the elastic rod in the various retaining clamps. At the end of growth, the implanted internal corrective appliance, which has become useless, has to be removed.

It is finally pointed out that the clearance or play of the elastic restoring structure in the different retaining flanges 9, 17 permits the normal growth of the child and gives the complete appliance the flexibility required for the progressive correction of the deformity. Experience has shown that it is possible to permit a rachidial growth of 5 cm, without it being necessary to change the corrective appliance and replace it by another appliance of a larger size. This is a by no means unimportant advantage of the invention because, on average, this permits an increase in the overall size of the child by 20 cm.

What is claimed is:

1. A biocompatible mechanical assembly for the dynamic correction of rachidial deformities, wherein in the deformed part of the rachis which it is wished to correct is implanted the mechanical assembly comprising, a retaining clamp fixed onto each vertebra of the deformed area, in the angle formed by the spinous process and the lamina, each retaining clamp having at least one guidance opening from one side to the other parallel to the axis of the rachis; and at least one springlike elastic rod in the shape of the corresponding part of a normal rachis, the rod being introduced into the aforementioned guidance openings of the retaining clamps fixed to the vertebrae, the rod being immobilized in rotation in each guidance opening and immobilized in translation on only one of the retaining clamps, said elastic rod applying a force to graually move each vertebra in said deformed area into its normal rachis position.

2. An assembly for the dynamic correction of rachidial deformities according to claim 1, wherein each retaining clamp is fixed to the associated vertebra by direct screwing into the centro-lateral disk.

3. An assembly for the dynamic correction of rachidial deformities according to claim 1, wherein each retaining clamp is fixed to the vertebra with the aid of a screw which passes through the spinous process and is fixed to the other face thereof by a nut for applying a bearing plate.

4. An assembly for the dynamic correction of rachidial deformities according to claim 1, wherein each retaining clamp is fixed to the vertebra with the aid of a screw, which is screwed into the vertebral pedicle.

5. An assembly for the dynamic correction of rachidial deformities according to any one of the claims 1, 2, 3 or 4, wherein the cross-section of the guidance openings of the retaining clamps have a shape excluding the rotation of the elastic rod about its axis and more particularly chosen from oval or polyhedral shapes and rails and crosses.

6. An assembly for the dynamic correction of rachidial deformities according to claims 1, 2, 3 or 4 wherein the openings passing through the retaining clamps have, at their inlet and outlet, a flared or widened shape permitting the bending of the elastic rod between the guidance points.

7. An assembly of the dynamic correction of rachidial deformities according to claims 1, 2, 3 or 4 wherein the guidance openings have an oval cross-section, whereof the major axis is contained in a sagittal plane.

* * * * *